(12) United States Patent
Kim

(10) Patent No.: US 12,239,330 B2
(45) Date of Patent: Mar. 4, 2025

(54) SURGICAL PIN GUIDE

(71) Applicant: THE CATHOLIC UNIVERSITY OF KOREA INDUSTRY-ACADEMIC COOPERATION FOUNDATION, Seoul (KR)

(72) Inventor: Seok Jung Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 309 days.

(21) Appl. No.: 17/909,064

(22) PCT Filed: Dec. 22, 2020

(86) PCT No.: PCT/KR2020/018869
§ 371 (c)(1),
(2) Date: Sep. 2, 2022

(87) PCT Pub. No.: WO2021/177566
PCT Pub. Date: Sep. 10, 2021

(65) Prior Publication Data
US 2023/0087824 A1 Mar. 23, 2023

(30) Foreign Application Priority Data
Mar. 3, 2020 (KR) .................. 10-2020-0026537

(51) Int. Cl.
*A61B 17/17* (2006.01)
(52) U.S. Cl.
CPC ...... *A61B 17/1742* (2013.01); *A61B 17/1721* (2013.01)
(58) Field of Classification Search
CPC .................. A61B 17/1721; A61B 17/1742
See application file for complete search history.

(56) References Cited

U.S. PATENT DOCUMENTS 2,200,120 A * 5/1940 Nauth ............... A61B 17/1721
408/110
2,301,500 A * 11/1942 Anderson .......... A61B 17/1721
606/103
(Continued)

FOREIGN PATENT DOCUMENTS

JP 2004-358057 A 12/2004
KR 10-2005-0123111 A 12/2005
(Continued)

OTHER PUBLICATIONS

International Search Report for PCT/KR2020/018869, dated Apr. 19, 2021.

*Primary Examiner* — David W Bates
(74) *Attorney, Agent, or Firm* — Sughrue Mion, PLLC

(57) ABSTRACT

Disclosed is a surgical pin guide. To this end, the present invention provides a surgical pin guide including a guide fixed to an outer circumferential surface of a femur and configured to allow a center pin and a central pressure reducer of a drill handpiece to approach a necrotic region of an expanded area, a guide main body including a handle provided on an upper surface of a block, a center pin-guide hole horizontally pierced at a center of a front surface of the block, and a plurality of side pin-guide holes pierced at predetermined inclination angles with respect to the center pin-guide hole, arranged radially in the front surface of the block, and configured to meet the center pin-guide hole in a rear surface of the block, and a leading body configured to allow the guide main body to be detached from the guide and approach the necrotic region of the femoral head in a rotationally folded state.

5 Claims, 4 Drawing Sheets

(56) References Cited

U.S. PATENT DOCUMENTS

| | | | | |
|---|---|---|---|---|
| 2,531,734 | A | * | 11/1950 | Hopkins ............ A61B 17/1721 606/97 |
| 5,207,753 | A | * | 5/1993 | Badrinath ............ A61B 17/742 606/96 |
| 5,324,295 | A | * | 6/1994 | Shapiro ............... A61B 17/1714 606/86 R |
| 2010/0211074 | A1 | * | 8/2010 | Hansson ............ A61B 17/1721 606/64 |
| 2015/0066041 | A1 | * | 3/2015 | Kim ................... A61B 17/1721 606/96 |
| 2018/0296244 | A1 | * | 10/2018 | Kim ................... A61B 17/3472 |
| 2019/0029743 | A1 | * | 1/2019 | Rocci ................... A61B 17/742 |

FOREIGN PATENT DOCUMENTS

| | | |
|---|---|---|
| KR | 10-2011-0071432 A | 6/2011 |
| KR | 10-1176746 B1 | 8/2012 |
| KR | 10-2013-0140007 A | 12/2013 |
| WO | 2009/094239 A1 | 7/2009 |

\* cited by examiner

SURGICAL PIN GUIDE

CROSS REFERENCE TO RELATED APPLICATIONS

This application is a National Stage of International Application No. PCT/KR2020/018869 filed Dec. 22, 2020, claiming priority based on Korean Patent Application No. 10-2020-0026537 filed Mar. 3, 2020.

TECHNICAL FIELD

The present invention relates to a surgical pin guide.

BACKGROUND ART

In general, avascular necrosis of a femoral head refers to a disease in which the femoral head is dying because of the blockage of blood flowing to the femoral head.

The avascular necrosis occurs in progression as blood circulation disorders occur over a part of the femoral head or the entire femoral head because of several causes.

The avascular necrosis of the femoral head collectively refers to the disease that causes secondary osteoarthritis due destruction of a hip joint.

The methods of surgically treating the avascular necrosis of the femoral head are broadly classified into a method of saving the patient's joint and a method of replacing the patient's joint with an artificial joint.

The femoral perforation or central decompression is used during a surgical procedure of maintaining the original joint.

When the above-mentioned surgical procedure is used, the surgical procedure is performed to remove the necrotic region of the femoral head and then transplant stem cells while transplanting the patient's long bone.

This surgical procedure is performed by removing a healthy sponge bone from the patient's hip joint bone, removing the dead bone from the femoral head, and then pressing the bone.

If the use of the patient's long bone is not appropriate, a hip joint bone of another person is used.

When using the hip bones of another person, there is a problem that the physical adaptation time of the patient after surgery is longer.

On the other hand, if the patient's long bone is transplanted, the procedure time increases, and the pain in the patient after surgery may increase.

A tool for treating avascular necrosis of a femoral head in the related art pierces a drill hole to a necrotic region by using a drill and then couples a center pin into the drill hole.

A pressure reducer moves forward straight while being guided by the center pin and approaches the necrotic region while repeatedly sawing the femur, thereby finally removing the necrotic region.

Because it is impossible to remove the necrotic region having a size equal to or larger than an outer diameter of the pressure reducer, there is a technical problem in that the method using the pressure reducer is not suitable for the surgical procedure of removing a wide necrotic region even though this method is suitable for the surgical procedure of removing a narrow necrotic region.

DISCLOSURE

Technical Problem

An object of the present invention is to stably handle a guide main body for pressing and installing a center pin and a side pin to a necrotic region of a femoral head.

Another object of the present invention is to accurately perform an extraction process by introducing a pressure reducer, which comes into contact with an outer circumferential surface of a femur, to a stable position when a center pin and a guide pin are sequentially used.

Technical Solution

Disclosed is a surgical pin guide.

To this end, the present invention provides a surgical pin guide including: a guide fixed to an outer circumferential surface of a femur and configured to allow a center pin and a central pressure reducer of a drill handpiece to approach a necrotic region of an expanded area; a guide main body including: a handle provided on an upper surface of a block; a center pin-guide hole horizontally pierced at a center of a front surface of the block; and a plurality of side pin-guide holes pierced at predetermined inclination angles with respect to the center pin-guide hole, arranged radially in the front surface of the block, and configured to meet the center pin-guide hole in a rear surface of the block; and a leading body configured to allow the guide main body to be detached from the guide and approach the necrotic region of the femoral head in a rotationally folded state.

Advantageous Effects

According to the present invention, the guide main body is detached from the guide and becomes a point rotated state, which makes it possible to smoothly perform the process of pressing and installing the center pin and the side pin to the necrotic region of the femoral head.

According to the present invention, the pressure reducer, which comes into contact with the outer circumferential surface of the femur, enters the stable position when the center pin and the guide pin are sequentially used, which makes it possible to accurately perform the extraction process.

MODES OF THE INVENTION

Figure 1:
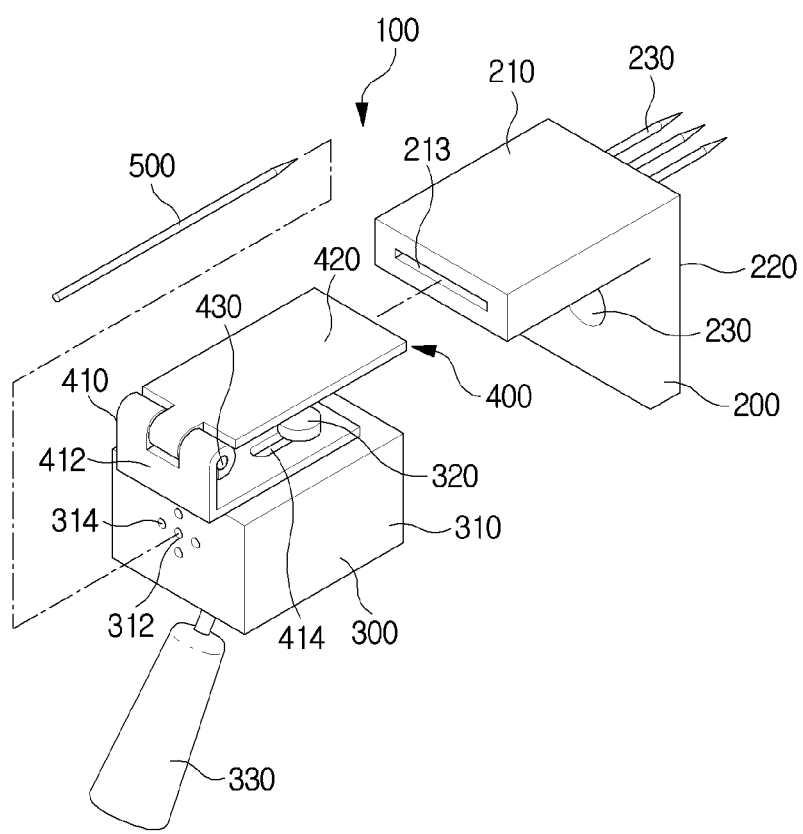
FIG. 1 is an exploded perspective view of a surgical pin guide for treating avascular necrosis of a femoral head to which the present invention is applied.

FIG. 1 is a perspective view illustrating a disassembled state of a surgical pin guide for treating avascular necrosis of a femoral head to which the present invention is applied.

A surgical pin guide 100 includes a guide 200 fixed to an outer circumferential surface of a femur C and configured to allow a center pin 500 and a central pressure reducer S of a drill handpiece T to approach a necrotic region of an expanded area so that an extraction process is performed at an accurate position.

A guide main body 300 includes a handle 330 and a block 310, and the handle 330 is suitable to set a position of the block 310 and is provided on an upper surface of the block 310 having a rectangular parallelepiped shape. A center pin-guide hole 312 is horizontally pierced at a center of a front surface of the block 310 and formed through a center of the rear surface of the block 310.

The center pin-guide hole 312 and side pin-guide holes 314 are formed in the block 310, and the side pin-guide holes 314 have the same diameter and are pierced at the periphery of the center pin-guide hole 312 pierced at the center of the front surface. The side pin-guide holes 314 are pierced at predetermined inclination angles.

The side pin-guide holes 314 are arranged radially in the front surface of the block 310 and pierced to be inclined at the predetermined inclination angles, such that the side pin-guide holes 314 meet the center pin-guide hole 312 in the rear surface of the block 310.

In addition, the surgical pin guide 100 includes a leading body 400 configured to allow the guide main body 300 to be detached from the guide 200 and approach the necrotic region of the femoral head in a state in which the guide main body 300 in a rotationally folded state.

The guide 200 includes a slot stand 210 to which the guide main body 300 is coupled or from which the guide main body 300 is separated.

A close-contact stand 220 is provided at an end of the slot stand 210 and extends in a vertical direction with respect to the outer circumferential surface of the femur.

A leading hole 250 is pierced in the close-contact stand 220 and prevents a tip of the central pressure reducer S of the drill handpiece T from swaying when the tip of the central pressure reducer S cuts and enters the necrotic region of the expanded area from the outer circumferential surface C of the femoral head.

The guide 200 has a slot 213 provided at a position opposite to fixing pins 230 configured to be fixed to the outer circumferential surface C of the femoral head, and the leading body 400 is coupled to or separated from the slot stand 210 by means of the slot 213.

The leading body 400 includes a first piece 410 configured to be inserted into the slot 213, and a second piece 420 coupled to the guide main body 300. The first piece 410 and the second piece 420 are connected to each other by means of a hinge pin 430.

The leading body 400 has a bent end 412 defined by bending a middle portion of the first piece 410 by a predetermined height so that the guide main body 300 is guided to the close-contact stand 220 of the guide 200 and separated from the close-contact stand 220.

The leading body 400 and the guide main body 300 are installed and connected as a support rivet 320 is installed on an upper surface of the block 310 through an operation hole 414 formed in the first piece 410 of the leading body 400.

When the guide main body 300 approaches the outer circumferential surface C of the femoral head, the rear surface of the guide main body 300 approaches and comes into close contact with the close-contact stand 220 of the guide 200 within a gap in the operation hole 414.

Figure 2:
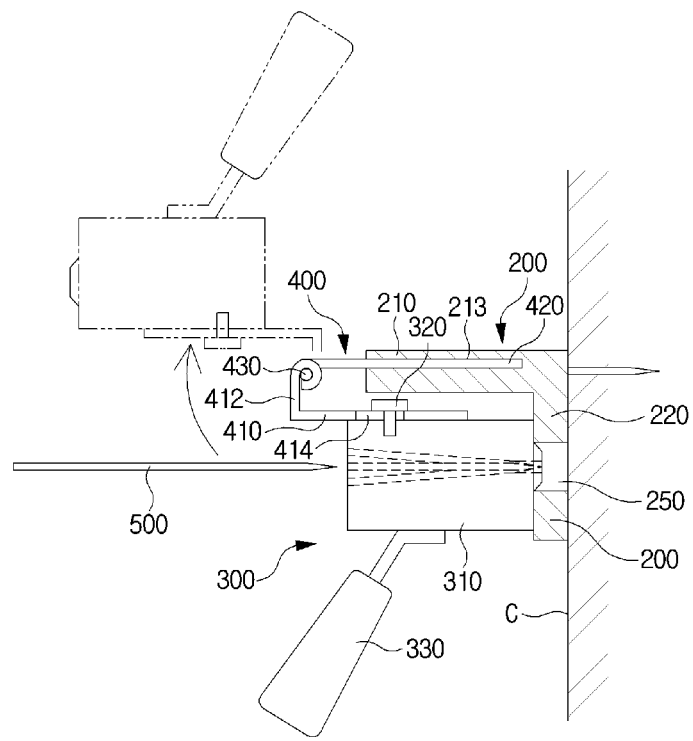
FIG. 2 is a view illustrating an operating state of the surgical pin guide for treating avascular necrosis of a femoral head to which the present invention is applied.

FIG. 2 illustrates an operating state of the surgical pin guide for treating avascular necrosis of a femoral head to which the present invention is applied.

When a necrotic region occurs around the femoral head C, a practitioner fixes the close-contact stand 220 of the guide 200 of the surgical pin guide 100 to a surgical position opposite to the necrotic region and prepares an extraction process.

The guide main body 300 is coupled to the guide 200 and allows the center pin, the side pin, and the central pressure reducer S of the drill handpiece T to enter the necrotic region.

To this end, the close-contact stand 220 of the guide 200 comes into contact with the surgical position of the femoral head C opposite to the necrotic region, and the fixing pins 230 are inserted into the femoral head C.

Thereafter, the second piece 420 of the connection body 400 installed on the guide main body 300 is inserted into the slot 213 formed in the slot stand 210 of the guide 200, and the guide main body 300 may rotate about the hinge pin 430 of the connection body 400.

When the guide main body 300 rotates about the hinge pin 430 from a rotationally folded state as demonstrated by the curved arrow and phantom lines in FIG. 2, the rear surface of the block 310 comes into contact with the surface of the close-contact stand 220 of the guide 200. In this case, the center pin-guide hole 312 is coincident with a central axis of the leading hole 250 pierced in the close-contact stand 220.

Thereafter, the practitioner holds the handle 330 with one hand and pushes the handle 330 so that the rear surface of the block 310 of the guide main body 300 come into close contact with the close-contact stand 220 of the guide 200.

The practitioner uses the other hand to press an end of the center pin 500 while inserting the center pin 500 into the center hole 312 formed in the front surface of the block 310 of the guide main body 300. Therefore, the tip of the center pin 500 is inserted into the position directed toward the surgical position of the femoral head C, such that the position is set to the surgical point.

Figure 3:
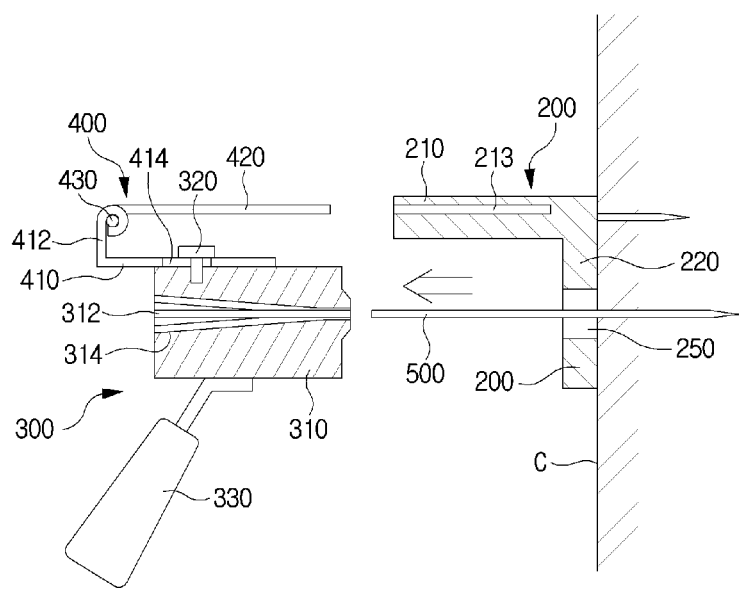
FIG. 3 is a view illustrating a state in which a guide main body is separated from a guide to which the present invention is applied.

FIG. 3 illustrates a state in which the guide main body is separated from the pin guide to which the present invention is applied.

When the center pin 500 enters the femoral head C through the center hole 312 formed in the block 310 of the guide main body 300 and through the leading hole 250 pierced in the close-contact stand 2 of the guide 200, a surgical procedure of moving the center pin forward toward the necrotic region is performed.

Because the central pressure reducer S of the drill handpiece T needs to be coupled to the center pin 500, the practitioner holds and pulls the leading body 400 connected to the guide main body 300.

When the leading body 400 is pulled, the second piece 420 is separated from the slot stand 210 of the guide 200, and the guide main body 300 is spaced apart from the close-contact stand 220 of the guide 200, such that the center pin 500 remains.

Figure 4:
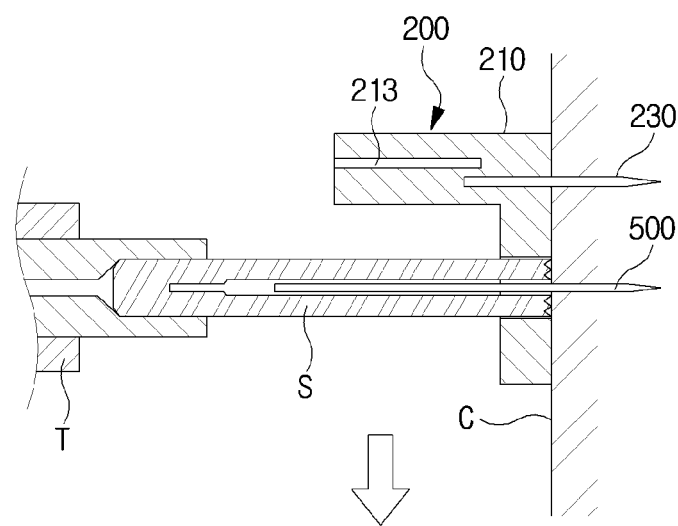
FIG. 4 is a view illustrating a state in which a central pressure reducer of the guide according to the present invention approaches and enters an outer circumferential surface of a femur.
Figure 4:
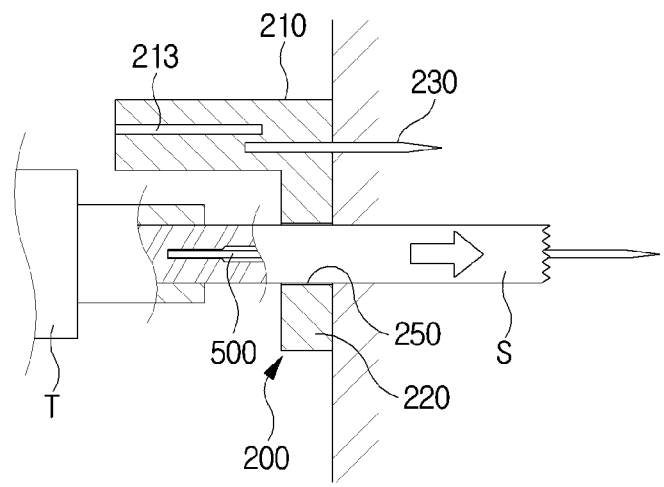
Figure 5:
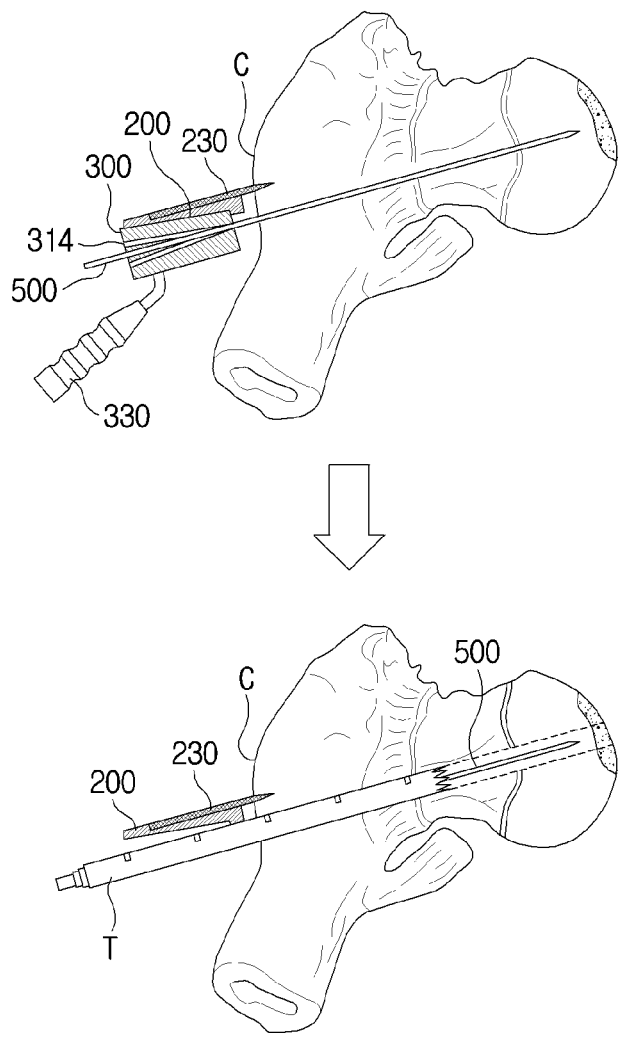
FIG. 5 is a front view illustrating a surgical procedure using the surgical pin guide for treating avascular necrosis of a femoral head according to the present invention.

FIG. 4 illustrates a state in which the central pressure reducer of the guide according to the present invention approaches and enters the outer circumferential surface of the femur.

The center pin 500 is inserted into the portion opposite to the surgical position of the femoral head C, such that in a state in which the surgical point is set, a length of a major part of the center pin 400 is exposed to the outer circumferential surface of the femoral head.

Therefore, to introduce the central pressure reducer S into the surgical position, the practitioner lifts the drill handpiece T and couples the mounted central pressure reducer S to a rear end of the center pin 500 so that a serrated end of the tip of the central pressure reducer S enters the leading hole 250 formed in the close-contact stand 220 of the guide 200.

The drill handpiece T operates after the serrated end of the tip of the central pressure reducer S enters the leading hole 250 formed in the close-contact stand 220 of the guide 200, such that the central pressure reducer S enters the surgical position from the outer circumferential surface of the femoral head by means of drilling of the serrated end.

A central portion of the necrotic region may be removed as the central pressure reducer S of the drill handpiece T enters the necrotic region by drilling. To remove the expanded area of the necrotic region, the central pressure reducer S of the drill handpiece T is pulled out in the entering direction and then inserted into the expanded area while entering the necrotic region again.

Because the second piece 420 of the leading body 400 connected to the guide main body 300 is inserted into the slot 213 formed in the slot stand 210 of the guide 200, the block 310 of the guide main body 300 is positioned at the initially assembled position again.

Next, the practitioner holds the handle 330 of the guide main body 300 with one hand, lifts the side pin, which is identical in shape to the center pin, with the other hand, and introduces the side pin into the side hole 314 formed in the block 310 of the guide main body 300.

When the side pin inserted into the side hole 314 in the block 310 exits the rear surface of the block 310, the side pin is spaced apart from the initial center hole by a predetermined inclination angle because of the inclination angle of the side hole, and the side pin is inserted into the outer circumferential surface of the femoral head C.

The position at which the side pin is inserted into the femur is included in the surgical position of the necrotic region of the expanded area to be removed.

Thereafter, the practitioner pulls the leading body 400 so that the guide main body 300 is separated from the slot stand 210 of the guide 200 and the side pin.

When the central pressure reducer S of the drill handpiece T is coupled to the side pin and moved forward toward the surgical position, the serrated end of the tip of the central pressure reducer S inclinedly drills the outer circumferential surface of the femoral head and extracts the necrotic region of the expanded area.

Because the leading hole 250 of the close-contact stand 220 of the guide 200 has a size equal to an outer diameter of the tip, i.e., the serrated end of the inserted central pressure reducer S, the leading hole 250 guides the tip of the central pressure reducer S so that the central pressure reducer S does not sway when the central pressure reducer S begins to rotate. Therefore, it is possible to perform an accurate surgical procedure on the surgical position of the necrotic region of the expanded area.

The guide main body 300 is mounted on the slot stand 210 of the guide 200 by the leading body 400 when the center pin and the side pin are sequentially installed on the outer circumferential surface opposite to the surgical position of the femoral head. Therefore, surgical tools for installing the pins may be easily handled.

The coupling implemented by the leading body 400 restricts the swaying of the guide main body 300. Therefore, it is possible to perform a surgical procedure that accurately approaches the initial surgical position.

The invention claimed is:

1. A surgical pin guide comprising:
   a guide configured to be fixed to an outer circumferential surface of a femur and configured to allow a center pin and a central pressure reducer of a drill handpiece to approach a necrotic region of an expanded area;
   a guide main body including: a handle provided on an upper surface of a block; a center pin-guide hole horizontally pierced at a center of a front surface of the block; and a plurality of side pin-guide holes pierced at predetermined inclination angles with respect to the center pin-guide hole, arranged radially in the front surface of the block, and configured to meet the center pin-guide hole in a rear surface of the block; and
   a leading body configured to allow the guide main body to be detached from the guide and approach the necrotic region of the femoral head in a rotationally folded state.

2. The surgical pin guide of claim 1, wherein the guide comprises:
   a slot stand to which the guide main body is coupled or from which the guide main body is separated;
   a close-contact stand extending from an end of the slot stand in a vertical direction with respect to the outer circumferential surface of the femur; and
   a leading hole pierced in the close-contact stand and configured to prevent swaying of a serrated end of the central pressure reducer of the drill handpiece that enters the necrotic region of the expanded area of the circumferential surface of the femur outer.

3. The surgical pin guide of claim 2, wherein the guide has a slot formed in the slot stand so that the leading body is coupled to or separated from the slot.

4. The surgical pin guide of claim 3, wherein the leading body comprises:
   a first piece configured to be inserted into the slot; and
   a second piece coupled to the guide main body, and
   wherein the first piece and the second piece are connected by a hinge pin.

5. The surgical pin guide of claim 4, wherein the leading body has a bent end defined by bending a middle portion of the first piece by a predetermined height so that the guide main body is guided by the close-contact stand of the guide and separated.

* * * * *